United States Patent [19]
Lawes et al.

[11] Patent Number: 5,080,675
[45] Date of Patent: Jan. 14, 1992

[54] TIBIAL COMPONENT FOR A REPLACEMENT KNEE PROSTHESIS

[76] Inventors: Peter Lawes, "Kingsmede", 118 Laburnham Road, Maidenhead, Berkshire SL6 4DB; Alan M. Ashby, 176 Bath Road, Maidenhead, Berkshire SL6 4LD; William A. Wallace, "High Trees", Foxwood Lane, Woodborough, Nottingham NG14 6ED, all of England; Akiho Hoshino, Room No. 405, 32-2 Narimasu, Itabashi-ku, Tokyo 175, Japan; Pier G. Marchetti, Via Le Aldini 94, 40136 Bologna; Maurilio Marcacci, Via Casaglia 15, 40135 Bologna, both of Italy

[21] Appl. No.: 664,710

[22] Filed: Mar. 5, 1991

[30] Foreign Application Priority Data

Mar. 12, 1990 [GB] United Kingdom ............... 9005496

[51] Int. Cl.⁵ ............................................. A61F 2/38
[52] U.S. Cl. .......................................... 623/20; 623/18
[58] Field of Search ...................... 623/20, 18, 16

[56] References Cited

U.S. PATENT DOCUMENTS

| | | | |
|---|---|---|---|
| 4,085,466 | 4/1978 | Goodfellow et al. | 623/20 |
| 4,340,978 | 7/1982 | Buechel et al. | 623/20 |
| 4,586,933 | 5/1986 | Shoji et al. | 623/20 |
| 4,711,639 | 12/1987 | Grundei | 623/20 |
| 4,714,474 | 12/1987 | Brooks, Jr. et al. | 623/20 |

FOREIGN PATENT DOCUMENTS

| | | | |
|---|---|---|---|
| 1191301 | 8/1985 | Canada | 623/20 |
| 0121421 | 10/1984 | European Pat. Off. | |
| 1534263 | 11/1978 | United Kingdom | 623/20 |
| 2061730 | 5/1981 | United Kingdom | 623/20 |

*Primary Examiner*—Ronald Frinks
*Attorney, Agent, or Firm*—Peter C. Richardson; Lawrence C. Akers; Raymond W. Augustin

[57] ABSTRACT

A tibial component for a replacement knee prosthesis comprising a tibial tray for connection to a suitably prepared tibia has a tray carrying fixed lateral and medial condylar bearing components. Only the medial component has a shock absorber located beneath it.

8 Claims, 4 Drawing Sheets

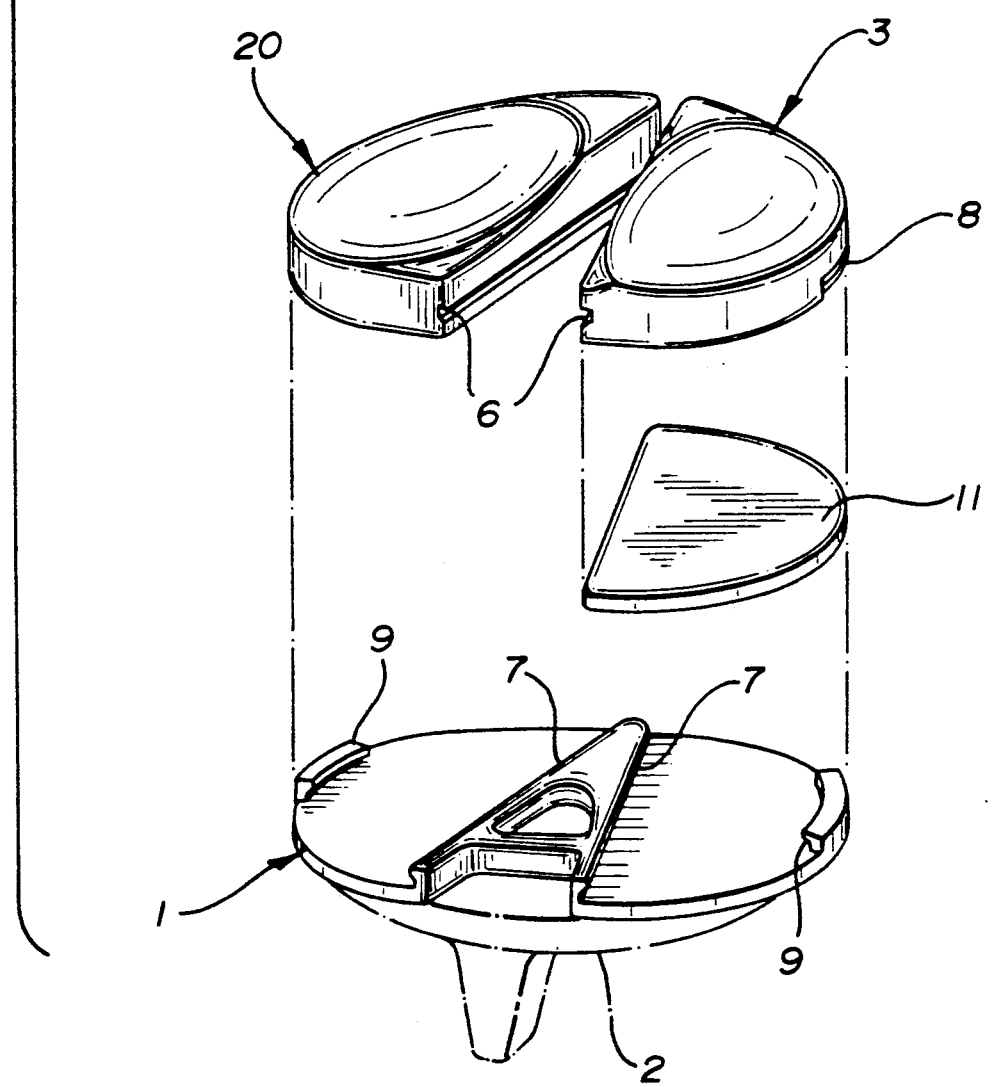

TIBIAL COMPONENT FOR A REPLACEMENT KNEE PROSTHESIS

BACKGROUND OF THE INVENTION

1. Field of the Invention

This invention relates to a tibial component for a replacement knee prosthesis and to a total knee prosthesis incorporating such a tibial component.

2. Description of the Prior Art

It is known to provide shock absorbers in total joint prostheses as shown, for example, in European Patent Application No. 83033081 (Publication No. 0 466 926) in which impact absorbers are provided on the tibial component. The impact absorbers are provided across the tibial component to provide shock absorbing for both the medial and lateral bearing components.

It is also known to provide menisci, that is to say, moving plastic components typically made of polyethylene between a metal tibial tray and a metal femoral component that are not locked in place as normal plastic tibial condyles are. Some examples are shown in U.S. Pat. Nos. 4,085,466, 4,340,978 and 4,586,933, and United Kingdom Patent Application No. 7937163 (Publication No. 2 061 730), British Patent Specification No. 1 534 263 In all these constructions both the medial and lateral condylar bearing components are arranged as menisci which can move.

Analysis of removed total knee components (removed for any reason whatsoever, i.e. pain, loosening, breakage, wear, etc.) has shown that damage occurs to a much greater degree in the medial compartment of the tibial bearing surface than the lateral. Biomechanical publications have for some time claimed that the loading in the medial condyle is very much higher than in the lateral condyle.

Similarly, an analysis of used knee implants and biomechanical studies all shown that as rotation occurs in the tibia, the fore and aft sliding occurs to a greater degree in the lateral compartment than it does in the medial.

SUMMARY OF THE INVENTION

It is an object of the present invention to provide a tibial component for a replacement knee prosthesis comprising a tibial tray for connection to a suitably prepared tibia. The tray carries both fixed lateral and medial condylar bearing components but with only the medial component having a shock absorber located beneath it.

In a first embodiment of the tibial component a stiffening element is provided between the shock absorber and the fixed medial condylar bearing component. . It is another object of the present invention to provide a tibial component for a replacement knee prosthesis having a tibial tray for connection to a suitably prepared tibia. The tray carries a fixed medial condylar bearing component and a movable lateral meniscal bearing component which can slide with anterior and posterior movement in relation to the tray.

If desired, some degree of medial or lateral movement can also be allowed in plane rotation relative to the tray. This has the advantage that it affords a lower constraint on the articulation, reducing the loads that can be transferred via it to the tibial tray and ultimately the bone fixation interface, and allowing the bearing to adopt the optimum position for maximum contact area with the condyles of the femoral component.

The fixed medial bearing component can be provided with a shock absorber beneath it, and if desired, a stiffening element can also be provided between the shock absorber and the medial bearing component. Again, the movable lateral meniscal bearing component can be provided with a shock absorber beneath it which can again have the stiffening element.

The invention also includes a total knee prosthesis for surgical replacement of a knee joint incorporating a tibial component as set forth above.

The invention has various advantages. Firstly, during normal human motion the femur slides, rolls and glides around the tibia, but to achieve this normal motion with a prosthesis means that the contact between the metal femoral shell and the plastic tibial bearing surface is very small. There cannot be close conformity between the geometry of the femoral condyle and tibial condyle. If there were close conformity then the fore and aft sliding could not occur except by the femoral bearing surface riding over the rim of the plastic. However, when there is point contact between the two, the wear rate and potential for fracture of the plastic can be relatively high.

Secondly, as the fore and aft movement occurs in a highly conforming or semi-conforming design, the fore and aft shear forces acting on the tibial component can be very high, causing it to become loose within the bone. Therefore, the introduction of prosthetic menisci allows there to be close conformity between the femoral component and the mating plastic surface, and yet the plastic component is free to slide around and not impart high horizontal forces on the tibial fixation interface. These horizontal forces are therefore transmitted from bone to bone, not through the prosthesis but via the interconnecting ligaments.

Unfortunately, a tibial component having two menisci free to move around causes the ligaments to have greater loads placed on them than is normal in the original anatomical joint. Furthermore, the implant is more likely to dislocate if one of the plastic menisci pops out. The invention described here by fixing the medial condyle and allowing the lateral condyle to move is claimed to be a better compromise. There is not such freedom for the totally unconstrained movement provided by a double meniscal joint. Because little fore and aft sliding is required on the medial compartment, there can be greater surface conformity (in the limit a partial sphere on a sliding partial sphere) designed into the prosthesis. The lateral meniscal compartment can also have a highly conforming bearing design. Some of the horizontal shear forces can be transmitted by the medial fixed condyle. It is expected that this design of knee will be less prone to loosening and less demanding on the ligaments than an implant with two sliding plastic menisci.

These and other objects and features of the present invention will become apparent from the following detailed description considered in connection with the accompanying drawings, which disclose several embodiments of the invention. It is to be understood that the drawings are to be used for purposes of illustration only, and not as a definition of the limits of the invention.

BRIEF DESCRIPTION OF THE DRAWINGS

The invention can now be performed in various ways and some embodiments will now be described by way of example and with reference to the accompanying drawings in which similar reference numerals denote similar elements throughout the several views:

FIG. 9 is a view similar to FIG. 1 of an embodiment having a fixed lateral and medial condylar bearing components and incorporating a shock absorber of the present invention.

DESCRIPTION OF THE PREFERRED EMBODIMENT

Figure 1:
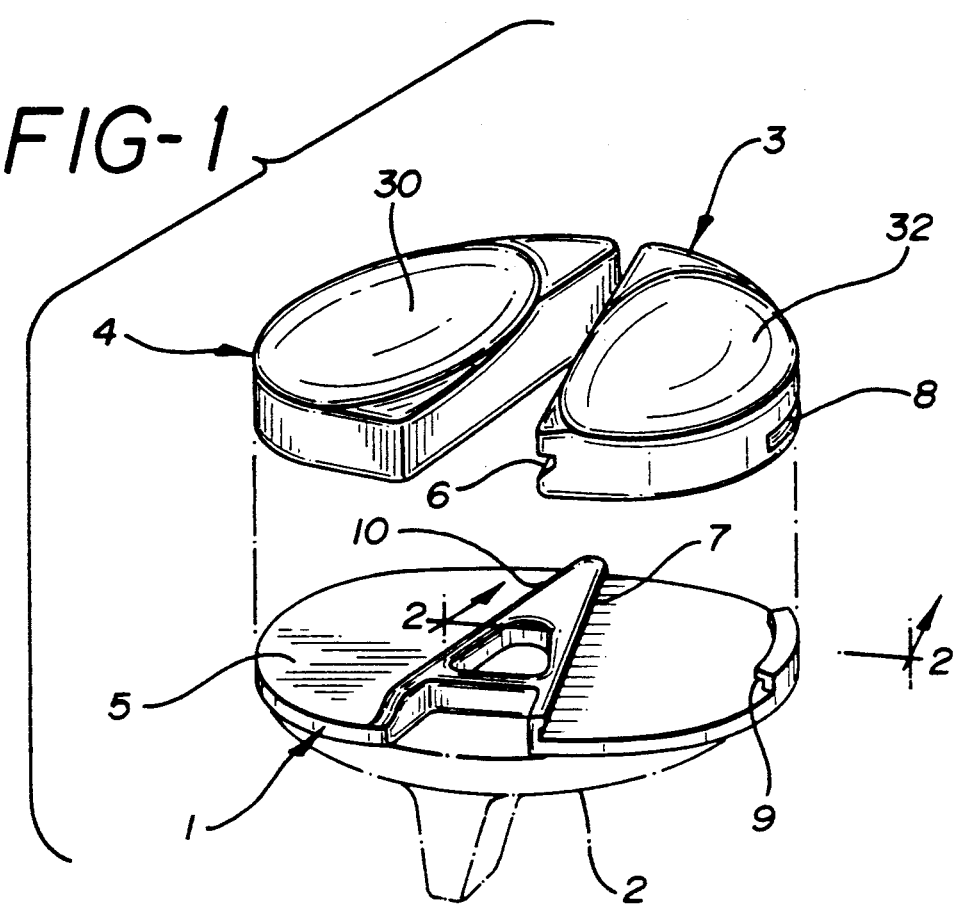
FIG. 1 is a diagrammatic isometric exploded view of a tibial component of the present invention provided with a movable lateral meniscal bearing component.
Figure 2:
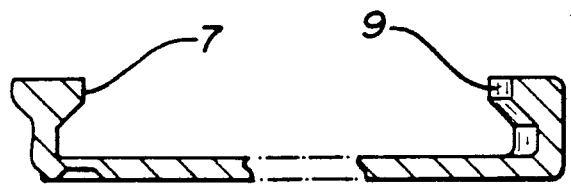
FIG. 2 is a partial cross-sectional view through the medial side of the tibial tray.

Referring to FIG. 1 and FIG. 2 there is shown a tibial component for a replacement knee prosthesis comprising a tibial tray 1 provided with an optional fixation peg, indicated by broken lines 2, for connection to a suitably prepared tibia. In the preferred embodiment, the tray 1 carries a fixed medial condylar bearing component 3 and a movable lateral meniscal bearing component 4 which can slide with anterior and posterior movement in relation to the tray 1. Component 4 can be allowed some freedom for medial and lateral movement and for rotation in the plane parallel to the top of tray 1. The uni-condylar meniscus provided by bearing component 4 is fully floating on the upper surface 5 of tray 1, but medial bearing component 3 is held in position by an anterior posterior slot 6 which engages a rail 7 on the tray 1. The other side of the bearing component 3 is provided with a groove 8 which can be snapped beneath a detent 9 on tray 1. Thus, the bearing component is first fitted onto the rail 7 and then snapped into position on the other side. The upper surface 5 of the tibial tray 1 is polished and is provided with an intracondylar retaining wall 10 of predetermined height.

The bearing surface 30 on the bearing component 4 exactly matches the distal surface of the femoral component (not shown), be that spherical or toroidal or some other form generated by driving the sectional form around the sagittal plane section of the femoral form. The bearing surface 32 on the fixed component 3 may also be toroidal or spherical or some form equivalent to the distal form of the femoral component geometrically modified to introduce the required lack of conformity to allow the components to move by rotation, gliding and sliding to reproduce the physiological kinematics of the knee. The bearing components are typically made from ultra-high molecular weight polyethylene.

Figure 3:
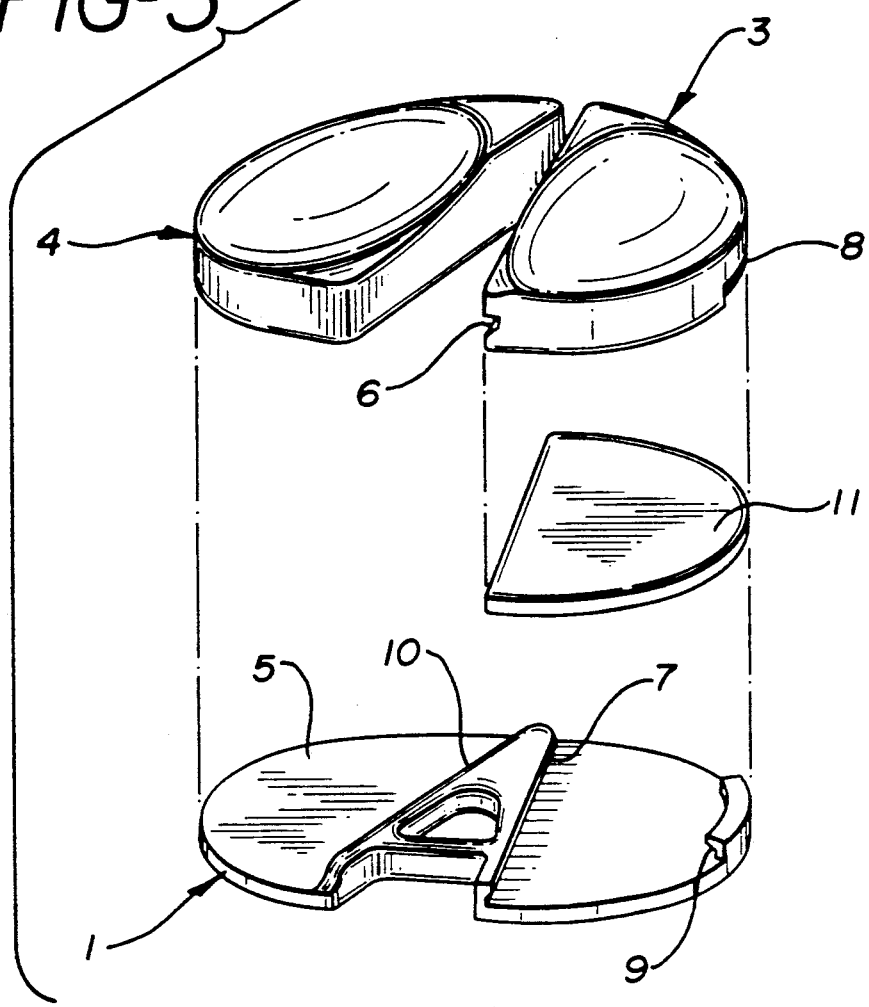
FIG. 3 is a view similar to FIG. 1 but showing a second embodiment of a shock absorber of the present invention.

The construction shown in FIG. 3 is somewhat similar to FIG. 1 and the same reference numerals are used to indicate similar parts, although in this figure the lower part 2 of tray 1 is not shown. As will be seen from FIG. 3 the fixed medial bearing component 3 is of a reduced thickness to accommodate a shock absorber 11 which is of substantially the same plan form as the component 3 but is made from a suitable compliant material such as rubber or a foamed elastomer. The use of the interpositional compliant materials forms a shock attenuation effect on the medial bearing component 3.

Figure 4:
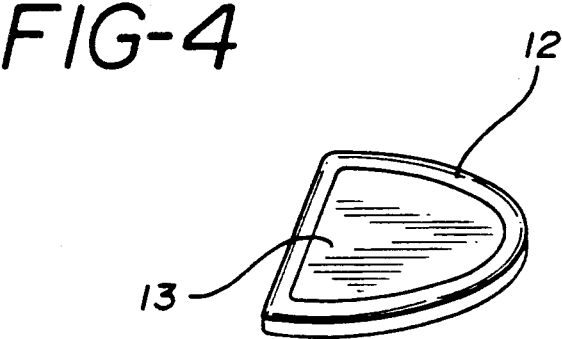
FIG. 4 is a diagrammatic isometric view of an alternative form of shock absorber embodying a stiffening element.

FIG. 4 shows a modified construction of shock absorber indicated by reference numeral 12. In this construction a stiffening element 13 is provided on the upper surface. This stiffening element is in the form of an interpositional metal tray which, when in position, is between the shock absorbing elastomeric layer and the ultra-high molecular weight polyethylene of bearing component 3. The advantage of this feature is the protection of the plastic bearing from off-set support loads and excessive deformation during articulation, which could compromise the fatigue strength and wear life of the component. A further benefit is that the metal interpositional tray provided by the stiffening element 13 allows the assembly of the shock absorbing and bearing components inter-operatively by the surgeon.

Figure 5:
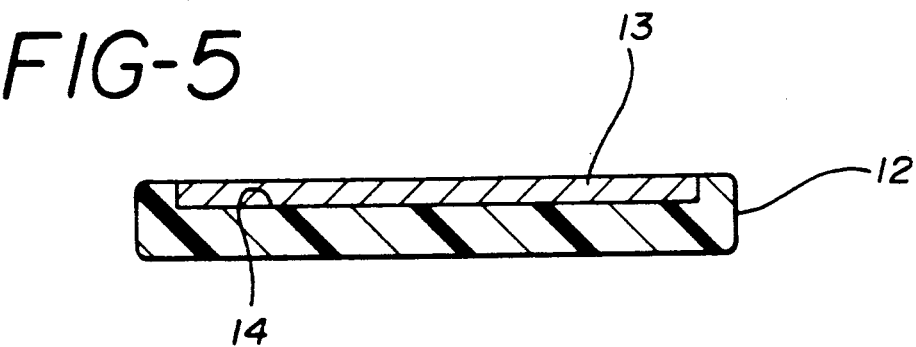
FIGS. 5, 6, 7 and 8 are cross-sectional elevational views through further alternative shock absorber constructions.
Figure 6:
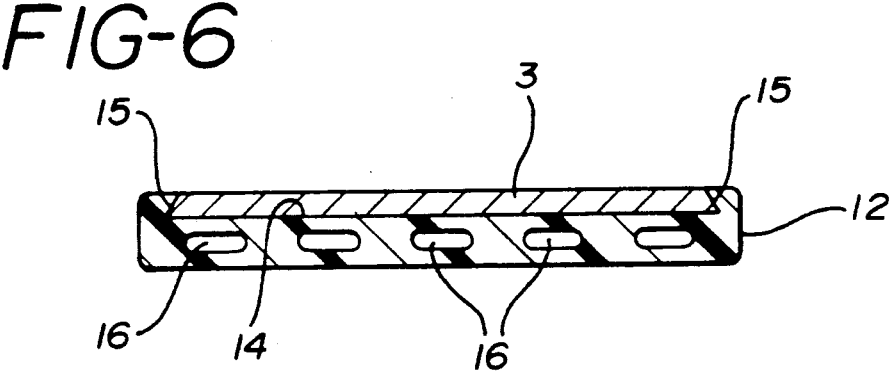

Some alternative constructions for shock absorbers incorporating a stiffening element 13 are shown in FIGS. 5, 6, 7 and 8. In FIG. 5 the stiffening element 13 is held by adhesive and/or by being arranged to be a press-fit into a depression 14 in the upper surface of the element. FIG. 6 shows a construction in which the stiffening element 13 is again located in a depression 14 but in this case the side edges 15 are undercut. This figure also illustrates the use of voids 16 in the elastomeric material.

Figure 7:
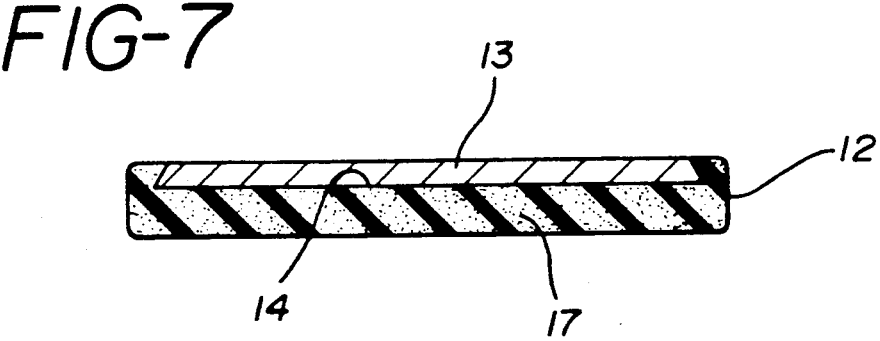

FIG. 7 shows a somewhat similar construction to FIG. 6, but in this case the shock absorber is made by a foamed elastomer indicated by reference numeral 17.

Figure 8:
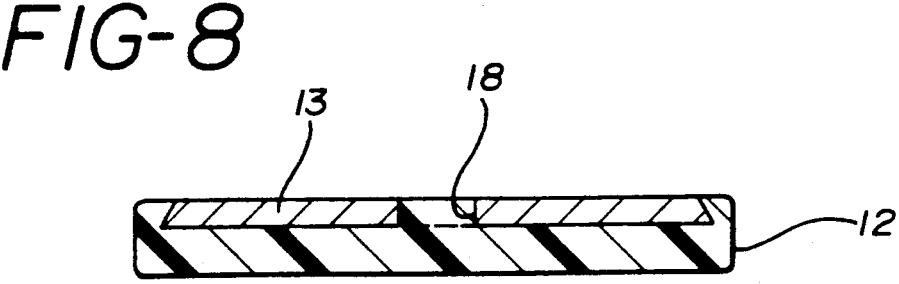

FIG. 8 shows an enhanced interlocking arrangement between the metal stiffening element 13 and the elastomer by countersunk holes, for example, indicated by reference numeral 18, or slots.

In the preferred constructions shown in FIGS. 3 to 8, a shock absorber is only provided beneath the fixed medial bearing component 3. However, if desired, shock absorbers of a similar type could also be provided beneath menisci bearing component 4. Thus a construction can be designed so that there can be shock absorbers in both the medial compartment and the lateral compartment and if the surgeon wishes not to use a lateral meniscus then he could have a medial shock absorber and a lateral compartment without either sliding or shock absorption.

As mentioned above, it will be appreciated that the material of the shock absorber can incorporate voids or foaming or other features, for example, shear loading arranging or other isovolumetric deformation mechanisms to adjust the compliance of this inter-layer.

FIG. 9 shows a construction in which similar reference numerals are used to indicate similar parts as in FIG. 3 but with this arrangement the lateral bearing component 20 is of similar construction to medial fixed bearing component 3. Bearing component 20 is also intended to be fixed in tray 1 and is therefore also provided with a slot 6 and a groove 8. Tray 1 has an additional detent 9 and rail 7 to allow the fixed lateral bearing component 20 to be snapped into position in a similar manner to medial bearing component 3. It will be seen, however, that the bearing component 20 is thicker than bearing component 3 because it does not have shock absorber 11 beneath it and both bearing components are therefore fixed but a shock absorber is only provided beneath the medial component. The construction of this shock absorber can be as described with regard to FIGS. 4 to 8.

While several examples of the present invention have been described, it is obvious that many changes and modifications may be made thereunto, without departing from the spirit and scope of the invention.

We claim:

1. A tibial component for a replacement knee prosthesis comprising a tibial tray for connection to a suitably prepared tibia, said tray carrying fixed lateral and medial condylar bearing components, only said medial component having a shock absorber located beneath it.

2. The tibial component for a replacement knee prosthesis as claimed in claim 1 in which a stiffening element is provided between the shock absorber and the fixed medial bearing component.

3. A tibial component for a replacement knee prosthesis comprising a tibial tray for connection to a suitably prepared tibia, said tray carrying a fixed medial condylar bearing component and a movable lateral meniscal bearing component which can slide with anterior and posterior movement in relation to said tray.

4. The tibial component for a replacement knee prosthesis as claimed in claim 3 in which medial or lateral movement of said movable lateral bearing component is allowed in plane rotation relative to said tray.

5. The tibial component for a replacement knee prosthesis as claimed in claim 3 in which said fixed medial bearing component is provided with a shock absorber beneath it.

6. The tibial component for a replacement knee prosthesis as claimed in claim 5 in which a stiffening element is provided between the shock absorber and the medial bearing component.

7. The tibial component for a replacement knee prosthesis as claimed in claim 6 in which said movable lateral meniscal bearing component is provided with a shock absorber beneath it.

8. The tibial component for a replacement knee prosthesis as claimed in claim 7 in which a stiffening element is provided between the shock absorber and the movable lateral meniscal bearing component

* * * * *